United States Patent [19]

Tokumitsu et al.

[11] 4,089,888
[45] May 16, 1978

[54] METHOD FOR PRODUCING A POLYCARBONATE OLIGOMER

[75] Inventors: Ichiro Tokumitsu; Hideo Konuma; Shigeaki Mochizuki; Kohichi Morotomi; Norio Murai; Mikio Koyama, all of Tokuyamashi, Japan

[73] Assignee: Idemitsu Petrochemical Co. Ltd., Tokyo, Japan

[21] Appl. No.: 704,209

[22] Filed: Jul. 12, 1976

[51] Int. Cl.$^2$ ............................................. C07C 68/02
[52] U.S. Cl. .................................................. 260/463
[58] Field of Search ......................................... 260/463

[56] References Cited

U.S. PATENT DOCUMENTS

| 2,335,441 | 11/1943 | Pearson et al. | 260/463 |
| 3,248,365 | 4/1966 | Oxenrider et al. | 260/463 |
| 3,631,200 | 12/1971 | Nehring et al. | 260/463 |
| 3,646,102 | 2/1972 | Kobayashi et al. | 260/463 |
| 3,974,126 | 8/1976 | Narita et al. | 260/463 |

Primary Examiner—Joseph Paul Brust
Assistant Examiner—Molly C. Eakin
Attorney, Agent, or Firm—Fred Philpitt

[57] ABSTRACT

Polycarbonate oligomer having uniform qualities is prepared by reacting an aqueous alkaline solution of 2,2-(4,4'-dihydroxydiphenyl) propane with phosgene in the presence of methylene chloride and as a characteristic point of this method, in the presence of an inert gas in an amount of 1 to 10 mol % based upon the phosgene.

3 Claims, No Drawings

METHOD FOR PRODUCING A POLYCARBONATE OLIGOMER

DESCRIPTION OF THE INVENTION

This invention relates to a method for producing polycarbonate oligomers having uniform qualities. More particularly, this invention relates to an improvement in the method for producing polycarbonate oligomer by reacting an aqueous alkaline solution of 2,2-(4,4'-dihydroxydiphenyl) propane (hereinafter abbreviated as bisphenol A) with phosgene in the presence of methylene chloride which comprises carrying out the reaction in the presence of 1 to 10 mol % of an inert gas based upon the phosgene.

As method for producing high molecular weight linear polycarbonate through one step reaction, there has heretofore been known a method in which an aqueous alkaline solution of 4,4'-dihydroxydiaryl-alkane such as bisphenol A with phosgene in the presence of an inert organic solvent such as methylene chloride, a tertiary amine as a polymerization catalyst, and an organic monohydroxy compound as a chain terminator.

According to this method, however, it is difficult to obtain products having uniform qualities on account of the difficulty of removal of reaction heat in forming polycarbonate oligomer during the reaction time and the difficulty of realizing stationary flow state of reaction liquid. This results in such a drawback that high molecular weight linear polycarbonate as final product exhibits a poor reproducibility of qualities. In order to overcome this drawback there has been proposed in Japanese patent publication No. 21460/1971, a method for producing polycarbonate oligomer having relatively uniform qualities which comprises introducing an aqueous caustic alkaline solution of a dihydroxy compound and an organic solvent for polycarbonate oligomer into a tubular reactor to form a mixed phase stream, and reacting it with phosgene in parallel flow to carry out removal of reaction heat effectively. If a polycarbonate oligomer having uniform qualities is obtained, it is easy to obtain various kinds of high molecular weight linear polycarbonate from the oligomer.

Noting this point, we have made comprehensive studies on the methods for producing polycarbonate oligomer having uniform qualities. As the result of these studies, we have discovered that when 1 to 10 mol % of inert gas based upon phosgene is present at the time of reaction of an aqueous alkaline solution of bisphenol A with phosgene in the presence of methylene chloride, a polycarbonate oligomer having much more uniform qualities can be obtained. The detail of the reason why the presence of an inert gas gives a preferable result is not yet known, but it is believed that the presence of a definite amount of inert gas probably reduces the pressure fluctuation in the reactor and this in turn greatly reduces the temperature change in the reaction part and tends to fix the reaction conditions at constant values.

The polycarbonate oligomer of the present invention consists of pentamer and less oligomers of bisphenol A, and its dimer is a principal component. It is a low molecular weight polycarbonate having an average molecular weight of 430 to 460 and an almost fixed amount of chloroformate radical.

In the production of polycarbonate oligomer by the reaction of an aqueous alkaline solution of bisphenol A with phosgene in the presence of methylene chloride, 1 to 10 mol % of an inert gas is caused to be present based upon phosgene, in the method of the present invention, but the inert gas referred to herein is the gas which is not reactive in the reaction of the present invention and shows gaseous state at temperatures of −30° to 170° C and under pressures of one to 10 atm. If the inert gas is less than 1 mol % or greater than 10 mol % based upon phosgene, not only the effectiveness of the present invention is not attained, but also the latter case leaves unreacted phosgene and hence is not preferable. It is possible to select the reaction temperature in the production of polycarbonate oligomer of the present invention from a broad range, but it is preferably in the range of from room temperature to 150° C.

If the resulting polycarbonate oligomer is reacted at room temperature for about two hours in a vessel type or tubular type reactor by adding, to its solution in methylene chloride, an aqueous solution of sodium hydroxide, an antioxidant such as sodium hydrosulfite, a chain terminator consisting of an organic monohydroxy compound such as paratertiary-butylphenol, and as a polymerization catalyst, a tertiary amine such as triethylamine and if necessary, bisphenol A, then various kinds of high molecular weight linear polycarbonates can be obtained, depending upon the addition conditions of the above-mentioned materials. Thus the resultant polycarbonate is purified by washing and finally separated from methylene chloride solvent to obtain products of high molecular weight linear polycarbonate.

The present invention will be illustrated more fully by way of specific examples and comparative examples which are not limitative of the present invention.

EXAMPLES 1-5

An aqueous solution consisting of 1,430 g of bisphenol A, 510 g of sodium hydroxide, 8,650 g of water and 1.43 g of sodium hydrosulfite as an antioxidant, 5,900 g of methylene chloride and a mixture of 865 g of phosgene with 1 to 10 mol % of carbon monoxide as an inert gas based upon phosgene, each per hour, were continuously fed to a tubular reactor constructed with two kinds of pipes connected (one having an inner diameter of 2 mm and a length of 4 m and positioned closer to the inlet and the other having an inner diameter of 6 mm and a length of 8 m and positioned closer to the outlet), and reaction was carried out at 30° C, whereby a solution of polycarbonate oligomer in methylene chloride was obtained.

The amounts of addition of inert gas and the results of properties of resultant polycarbonate oligomers are shown in Table 1.

COMPARATIVE EXAMPLES 1-5

In the above-mentioned specific examples, the amounts of addition of inert gas were changed to values less than 1 mol % and greater than 10 mol %, and methylene chloride solutions of polycarbonate oligomer were obtained. The amounts of addition of inert gas and the results of properties of resultant polycarbonate oligomer are shown also in Table 1.

Table 1

| | | Amounts of addition of Inert gas (mol %) | Average molecular weight of polycarbonate oligomer | Concentration of chloroformate radical in polycarbonate oligomer (mol/l) |
|---|---|---|---|---|
| Example | 1 | 1 | 460 | 1.10 |
| " | 2 | 3 | 450 | 1.10 |
| " | 3 | 5 | 440 | 1.15 |
| " | 4 | 8 | 430 | 1.20 |
| " | 5 | 10 | 430 | 1.20 |
| Comparative example | 1 | 0 | 500 | 0.90 |
| " | 2 | 0.5 | 490 | 0.98 |
| " | 3 | 0.9 | 470 | 1.10 |
| " | 4 | 11 | 420 | 1.20 |
| " | 5 | 15 | 300 | 1.50 |

As evident from this table, it is seen that by the presence of an inert gas in definite amounts, the resultant polycarbonate oligomers show approximately fixed values of average molecular weight and concentration of chloroformate radical and thus uniform qualities.

Even when nitrogen gas is substituted for carbon monoxide as an inert gas, approximately the same results were obtained as shown in the above-mentioned Table.

What is claimed is:

1. In the method for producing polycarbonate oligomers having an average molecular weight of 430–460 and a chloroformate radical concentration of 1.1 to 1.2 mol per liter of methylene chloride solution by introducing an aqueous alkaline solution of 2,2-(4,4'-dihydroxy-diphenyl) propane and methylene chloride into a tubular type reactor to form a mixed phase stream which is reacted with phosgene in a parallel flow, the improvement which comprises introducing one to 10 mol % of an inert gas based upon phosgene, together with phosgene into said tubular type reactor.

2. The method of claim 1 wherein said inert gas is carbon monoxide.

3. The method of claim 1 wherein said inert gas is nitrogen.

* * * * *